(12) United States Patent  
Ishikawa et al.

(10) Patent No.: US 6,306,081 B1
(45) Date of Patent: Oct. 23, 2001

(54) HOOD FOR AN ENDOSCOPE

(75) Inventors: Masahiro Ishikawa, Hino; Koichi Kawashima, Tokyo, both of (JP)

(73) Assignee: Olympus Optical Co., Ltd., Tokyo (JP)

( * ) Notice: Subject to any disclaimer, the term of this patent is extended or adjusted under 35 U.S.C. 154(b) by 0 days.

(21) Appl. No.: 09/293,141

(22) Filed: Apr. 16, 1999

(30) Foreign Application Priority Data

Apr. 21, 1998 (JP) .................................................. 10-110792

(51) Int. Cl.[7] ........................................................ A61B 1/00
(52) U.S. Cl. .................... 600/127; 600/115; 600/116; 604/96.01; 604/102.02
(58) Field of Search .................... 600/127, 116, 600/115, 129; 604/96.01, 102.02, 103

(56) References Cited

U.S. PATENT DOCUMENTS

| 3,833,004 | * | 9/1974 | Vazquez et al. | 128/349 |
|---|---|---|---|---|
| 3,866,599 | * | 2/1975 | Johnson | 128/2 |
| 4,284,081 | * | 8/1981 | Kasper et al. | 128/349 |
| 4,681,093 | * | 7/1987 | Ono et al. | 128/6 |
| 4,961,738 | | 10/1990 | Mackin . | |
| 5,725,545 | * | 3/1998 | Bircoll | 606/192 |
| 5,897,487 | * | 4/1999 | Ouchi | 600/127 |
| 5,915,383 | * | 6/1999 | Pagan | 128/207.15 |
| 5,976,073 | * | 11/1999 | Ouchi | 600/129 |

FOREIGN PATENT DOCUMENTS

| 55-19682 | 2/1980 | (JP) . |
|---|---|---|
| 9-66019 | 3/1997 | (JP) . |
| WO 94/11052 | 5/1994 | (WO) . |

* cited by examiner

Primary Examiner—Linda C. M. Dvorak
Assistant Examiner—Jocelyn Debra Ram
(74) Attorney, Agent, or Firm—Frishauf, Holtz, Goodman, Langer & Chick, P.C.

(57) ABSTRACT

A hood for an endoscope which is detachably mounted near a distal end portion of the endoscope. The hood has a balloon adapted to be expanded into a substantially cylindrical configuration by injecting a fluid into the balloon, and to be contracted by discharging the fluid out of the balloon. A visual field of the endoscope can be secured by expanding the balloon, and can be prevented from being shaded by contracting the balloon.

16 Claims, 2 Drawing Sheets

HOOD FOR AN ENDOSCOPE

BACKGROUND OF THE INVENTION

The present invention relates to a hood for an endoscope which is mounted on a distal end portion of an insertion section of the endoscope.

In the observation and surgical operation of the body cavity of a patient using direct-viewing type endoscope, an observation space and operation field have to be secured with an endoscope's hood attached to the distal end portion of an insertion section of the endoscope when the observation space and operation field in particular are narrower in a location such as the esophagus and duodinal bulb.

In a location, such as the stomach, where a broader observation space and operation field can be secured, the endoscope's hood attached to the distal end portion of the insertion section of the endoscope shades or blocks the observation space and operation field and it is difficult to perform proper procedure due to the presence of such a hood. It may be considered that, in such a case, a hood need be removed from the endoscope. At that time, the endoscope's hood has to be withdrawn out of the body cavity and removed from the endoscope, thus involving a cumbersome operation and more operation time. This gives an excessive burden to the operator and to the patient.

As shown in JPN UM APPLN KOKAI PUBLICATION NO. 55-19682, a hood unit has been proposed comprising a hood slidably mounted on the distal end portion of the insertion section of the endoscope, a spring means for urging the hood in an extending direction, a retaining mechanism for retaining the hood in a retracted position against the action of the spring means, and a string-like wire for releasing the retainment of the hood by the retaining mechanism, whereby the visual angle can be changed by moving the hood. Such a slidable system requires a mechanism for slidably moving the hood, a mechanism for retaining the hood in a retracted position, a retainment-releasing operation mechanism, etc., thus complicating the structure at a distal end portion of the endoscope.

JPN PAT APPLN KOKAI PUBLICATION NO. 9-66019 has proposed an endoscope having a hood at a distal end portion of an insertion section and a high-frequency snare wire anchored to the outer peripheral portion of the hood. The endoscope's hood in this case is fixedly mounted on the distal end portion of the insertion section. For this reason, the visual field is shaded at all times by a projected hood, thus lowering the observation capability.

BRIEF SUMMARY OF THE INVENTION

An object of the present invention is directed to, as required, secure a visual field using a hood, to prevent the shading of the visual field and enhance an observation capability and treating capability in accordance with the situations involved. The object of the present invention is achieved by an endoscope's hood as will be set out below.

That is, the present invention provides a hood mounted at and near a distal end portion of an insertion section of an endoscope, in which the hood has an annular balloon adapted to be expanded into a substantially cylindrical configuration by injecting a fluid and to be contracted by discharging the fluid.

The visual field can be secured using the hood expanding the balloon, and by contracting the balloon it is possible to prevent the visual field from being shaded by the hood. As a result it is possible to use the endoscope's hood in an optimal state according to the situation in which it is used. It is thus possible to enhance an observation capability and a processing capability.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

First Embodiment

Figure 1:
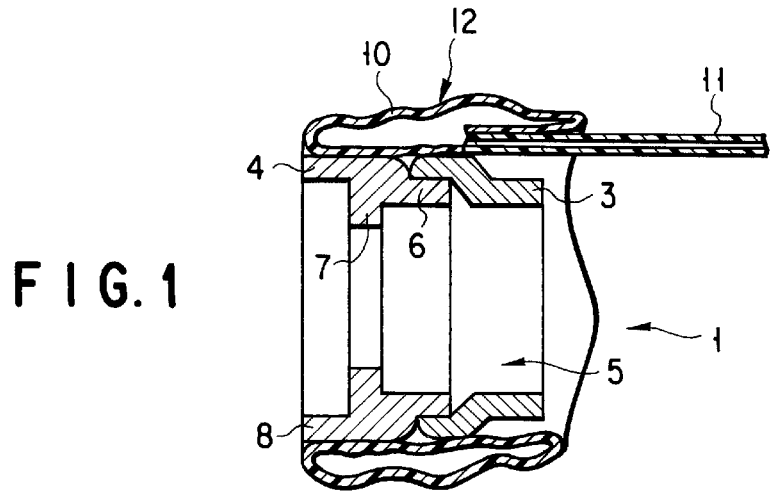
FIG. 1 is a vertical cross-section showing a hood for an endoscope according to a first embodiment of the present invention.

A first embodiment of the present invention will be explained below with reference to FIGS. 1 to 3.

A hood 1 of an endoscope has a substantially cylindrical mount member 3 mounted over an outer peripheral portion of a distal end section 2 of an insertion section of a direct-viewing type endoscope. The mount member 3 is intimately joined, adhesively bonded or threaded, for example, to the outer peripheral surface of the distal end portion 2 of the endoscope. A joining member 4 is, for example, bonded to the front end of the mount member 3. The mount member 3 and joining member 4 are integrally connected to provide a basic body (body member) 5. The joining member 4 determines the mount position of the endoscope's hood 1 relative to the distal end section 2 of the endoscope.

The joining member 4 is formed of an integral unit comprising a cylindrical section 6 equal in diameter to the mount member 3, a flange 7 abutting against an end face of the distal end section 2 of the endoscope and a hood section 8 continuous at a front end with the flange 7. The mounting position of the endoscope's hood 1 is determined by abutting the flange 7 against the front end face of the distal end section 2. That is, the joining member 4 determines the mount position of the endoscope's hood 1 relative to the distal end section 2 of the endoscope.

A balloon 10 has its inner side section fixedly mounted on the outer peripheral surface of the joining member 4 to be expandable in an annular configuration. Needless to say, the balloon 10 may be mounted over the outer peripheral surfaces of the mount member 3 and joining member 4.

Figure 2:
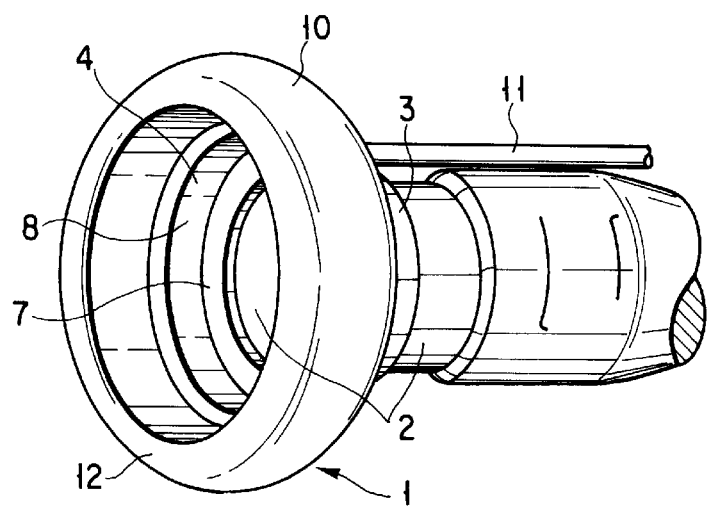
FIG. 2 is a perspective view showing a distal end portion of the endoscope which is equipped with the above-mentioned hood.

The balloon 10, upon being contracted, is set in a substantially cylindrical state as shown in FIG. 1. By injecting a fluid, such as a gas or physiological salt solution, into the balloon, the balloon is expanded into a substantially annular configuration as shown in FIG. 2. By discharging the fluid from an inner space of the balloon 10, the balloon 10 is contracted back into a state as shown in FIG. 1.

The balloon 10, being inflated, has its portion extended forward relative to the forward end of the hood section 8 and expanded into a substantially cylindrical state. Here, the balloon 10, before being expanded, is retracted out of a visual field of the endoscope and, being expanded, has its forward portion so extended as to obtain the visual field of the endoscope. Since the balloon 10 has its inner film-like portion joined to the outer peripheral portion of the basic body 5, even if the balloon 10 is expanded, the inner film-like portion is held in place and, in comparison with a free balloon type, the inside of the balloon 10 is not expanded to too large an extent.

As a material of the balloon 10 use is preferably made of a transparent resin film. As a material of the resin film it is preferred that, even under an application of any external force to the balloon when a forward end of the balloon is pushed against a mucous membrane, an expanded state stay not-simply collapsed. Such a practical material may be, for example, polyethyleneterephthalate or polynaphthaleneterephthalate.

To a back end of the balloon 10 a flexible tube 11 is connected as a supply/discharge tube. Through this tube 11, a fluid is injected into, and discharged out of, the balloon 10. The flexible tube 11 is connected to a proximal end side along an outer surface of the insertion section of the endoscope. The tube 11 serves both as a member for forming a passageway for injecting a fluid into the inner surface of the balloon 10 and as a member for forming a passageway for discharging the fluid out of the inner space of the balloon 10.

An explanation will be given below of how to use the endoscope's hood. First, as shown in FIG. 1, the balloon 10 is attached to the distal end section 2 of the endoscope. And with the balloon 10 set in a contracted state, the insertion section of the endoscope is inserted into the body cavity of a patient.

In the case where the body cavity with the insertion section of the endoscope so inserted is narrower in observation space or in an operation field and it is necessary to enlarge the observation space or operation field, the balloon 10 is expanded by an operation as will be set out below. That is, a fluid is injected through the tube 11 into the balloon 10. Then, as shown in FIG. 2, a pressure in the balloon 10 rises and is expanded into a hood-like configuration. The balloon 10, being so expanded, is extended outwardly into a rather hard hood as a whole and forcedly enlarges a surrounding wall to secure the observation space and operation field ahead of the forward end portion of the balloon 10. The forward end portion of the balloon 10 is not only outwardly enlarged but also forwardly extended to provide a hood area 12 around the forward area of the distal section 2 of the endoscope.

Even in the case where the observation space and operation field are narrower in the body cavity into which the insertion section of the endoscope is inserted, a greater observation space and operation field can be secured and such an observation of a region in the body cavity enables the biopsy as well as the removal, etc., of polyps by a high-frequency snare to be performed.

Further, in the case where the body cavity into which the insertion section of the endoscope is inserted is relatively wider, it is possible to use the balloon 10 in the contracted state. In this case, the balloon 10 is retracted back from the forward end of the insertion section of the endoscope, that is, from the position of the observation window and, without the observation field being shaded by the hood of the endoscope 1, it is possible to broadly secure the observation space and operation field in the body cavity of the patient and hence to secure a high observation capability.

In this way, the endoscope's hood 1 is extended and retracted back and the state of the hood 1 can be selected in accordance with the use to which it is put. And the examination, etc., under the microscope can be made in an optimal state.

In the case where the insertion section of the endoscope is pulled back from the body cavity of the patient, the fluid in the balloon 10 is discharged and, by doing so, the balloon 10 is contracted, so that these can be readily withdrawn in a manner which lessens the burden on the patient.

How a lesion 13 produced on the mucous membrane is removed, under the hood-equipped endoscope, by the use of a high-frequency snare will be explained below.

Figure 3:
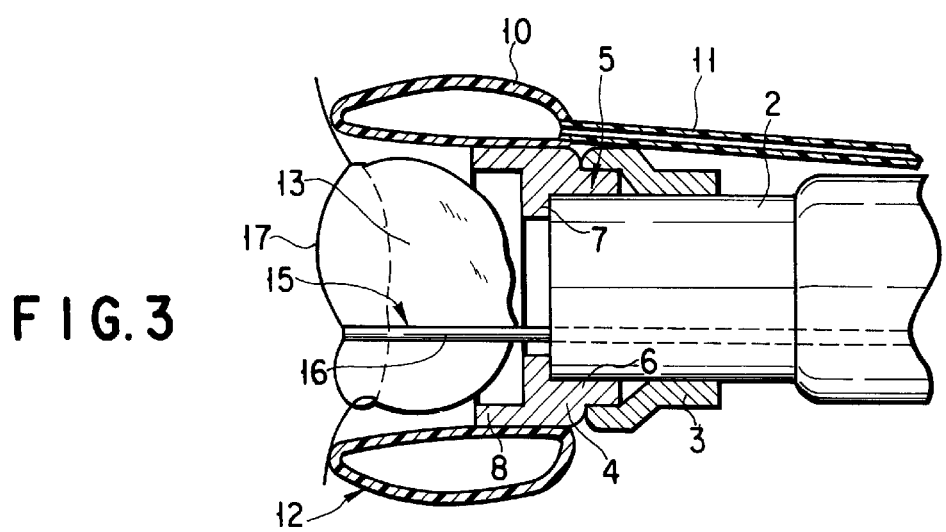
FIG. 3 is a vertical cross-section showing a distal end section of the endoscope which is equipped with the above-mentioned hood.

As shown in FIG. 3, the distal end section of the endoscope is inserted into the body cavity of the patient and moved nearer to a lesion 13 of the patient and the balloon 10 is expanded. Then the balloon 10, being expanded, is extended forward at the lesion 13 and the forward end edge of the hood 12 is abutted against the surrounding wall of the lesion 13. And a loop-like wire 17 attached to a sheath 16 of the high-frequency snare 15 inserted into a channel of the endoscope has its loop opened while being contacted with the inner surface of the forward end portion of the hood section 12.

As shown in FIG. 3, while the forward end edge of the hood section 12 is pushed against the surrounding wall of the lesion 13, a suction force is applied from a suction source, not shown, through the channel of the endoscope to provide a negative pressure in an area surrounded with the hood section 12. Then, the lesion 13 is sucked at an area around the annular hood section 12, so that it is raised as a greater polyp-like region.

At this time, the raised polyp-like region 13 is automatically surrounded by a previously opened loop-like snare wire 17 along the inner surface of the hood section 12.

The opened snare wire 17 is pulled back into the sheath section 16 and tightened at the root portion of the entrapped lesion 13. And a high-frequency current flows through the snare wire 17 to cut off the entrapped raised polyp-like lesion 13.

Since the expanded balloon 10 is strong enough to allow the lesion 13 to be inwardly held by the substantially cylindrical balloon 10 under an external force applied to the mucous membrane in the body cavity of the patient, it is possible to entrap the lesion 13 by this operation inwardly around the balloon 10.

Second Embodiment

Figure 4:
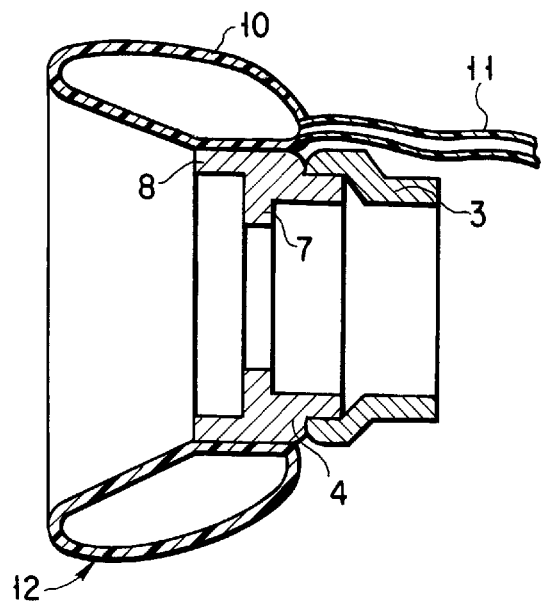
FIG. 4 is a vertical cross-section showing a hood for an endoscope according to a second embodiment of the present invention.

A second embodiment of the present invention will be explained below with reference to FIG. 4. FIG. 4 is a vertical cross-section showing a hood of an endoscope.

The second embodiment is different from the first embodiment in that, when the balloon 10 is expanded, the area of the forward flared open end is greater than that of the forward open end of the first embodiment. That is, when the balloon 10 is expanded, a hood section 12 is expanded in an outwardly flared configuration. The other structure of the second embodiment is the same as that of the first embodiment.

When the balloon 10 is expanded, the hood section 12 is enlarged in its diameter direction. In comparison with the first embodiment, a greater amount of mucous membrane can be removed when a lesion is cut off by a high-frequency snare 15.

Third Embodiment

Figure 5:
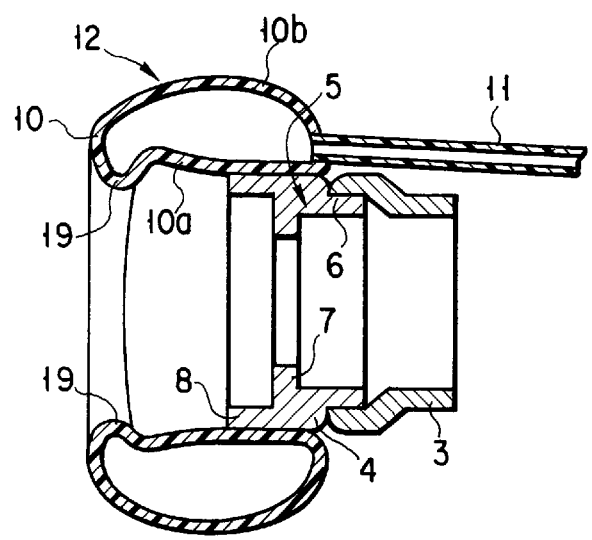
FIG. 5 is a vertical cross-section showing a hood for an endoscope according to a third embodiment of the present invention.
Figure 6:
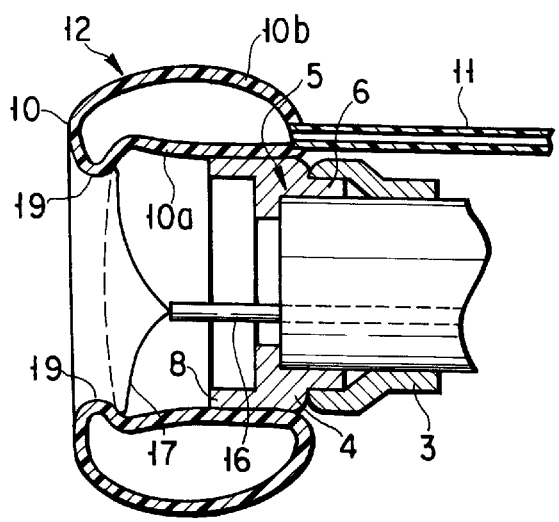
FIG. 6 is a vertical cross-section showing a distal end portion of the hood-equipped endoscope according to the third embodiment of the present invention.

A third embodiment of the present invention will be explained below with reference to FIGS. 5 and 6. The third embodiment is different from the first embodiment in that a portion of a balloon wall section 10a situated on the inner side of the balloon 10 is inelastic (as this material, use may be made of a polyethylene film or a polyethyleneterephthalate or polynaphthaleneterephthalate) and that a portion of a balloon section 10b situated on the outer side of the balloon 10 is elastic (as this material use may be made of a urethane film or silicone film).

According to this structure, when the balloon 10 of the endoscope's hood 1 is pushed against a lesion, since the outer side balloon wall section 10b b is elastic in nature, it can be softly applied to a mucous membrane without causing any damage to the mucous membrane. Further, the inner side balloon wall section 10a is inelastic and the shape of the balloon 10 is hard to collapse and the balloon is expanded to a desired configuration.

In the present embodiment, a small-diameter section 19 smaller than a main section of the inner side balloon wall section 10a is formed as a full-circle annular configuration at the forward end side of the balloon 10. According to the structure of the small-diameter section 19, as shown in FIG. 6, a snare wire 17 passed through the endoscope is opened and the opened snare wire 17 can be anchored at an inner side raised wall portion of the small-diameter section 19. That is, the opened high-frequency snare wire is anchored to the small-diameter raised annular section and held at that area.

By applying a suction force to a lesion 13 through the channel of the endoscope it is sucked into the hood 12 and the sucked-in lesion 13 is positively entrapped into an opened loop since the snare wire 17 is anchored to the raised small-diameter section 19 of the balloon 10. At that time, the loop is positively spread open and the lesion 13 can be squeezed at its root portion by an operation.

Here, according to the present invention, the raised small-diameter section 19 is provided at the forward end portion of the balloon and, even if being near the forward end, the above-mentioned advantage can be obtained. In this sense, for example, the small-diameter section may be provided at a location about 10 mm from the forward end backward toward a proximal end side.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A hood adapted to be mounted at a distal end portion of an insertion section of an endoscope, said hood comprising:
   a body member having an opening at a distal end side;
   an annular balloon mounted on the body member and having an inner space defined by an inner circumferential surface and an outer circumferential surface, said balloon being adapted to be expanded by injecting a fluid into the inner space so that at least an external diameter is enlarged and to be contracted by discharging the fluid out of the inner space so that the balloon is shrunk to a substantially cylindrical configuration; and
   at least one passageway through which the fluid may be injected into the inner space of the balloon, and through which the fluid may be discharged out of the inner space of the balloon;
   wherein said balloon comprises a rearward wherein a rearward portion of said inner circumferential surface of said balloon is connected to an outer peripheral surface of the body member at a position close to a forward end of the body member.

2. The hood according to claim 1, wherein the balloon comprises a transparent material.

3. The hood according to claim 1, wherein the balloon comprises a portion which, when the balloon is expanded by injecting the fluid into the inner space, extends forward relative to a forward end of the body member and is expanded into a substantially annular configuration so that an observation space and operation field can be secured.

4. The hood according to claim 3, wherein the portion of the balloon expanded into the substantially annular configuration is located out of a visual field of the endoscope before the balloon is expanded and enters into the visual field of the endoscope after the balloon is expanded.

5. The hood according to claim 3, wherein the portion of the balloon expanded into the substantially annular configuration defines an opening of greater diameter than a forward end opening of the body member when the balloon is expanded.

6. The hood according to claim 3, further comprising a small-diameter annular section formed on an inner side of a forward end opening of the portion of the balloon expanded into the substantially annular configuration, and wherein said small-diameter annular section is adapted to anchor a looped high-frequency snare wire and hold the wire in place.

7. The hood according to claim 1, further comprising a small-diameter annular section formed on an inner side of a forward end opening of the balloons and wherein when the balloon is expanded, the small-diameter annular section is adapted to anchor a high-frequency snare wire and hold the wire in place.

8. The hood according to claim 1, wherein the body member comprises a mount member adapted to be connected to the distal end portion of the insertion section of the endoscope, and a joining member that is connected to the mount member and to which the balloon is mounted.

9. The hood according to claim 8, wherein the balloon is joined to, and mounted on, an outer peripheral surface of the joining member of the body member.

10. The hood according to claim 1, wherein the at least one passageway through which the fluid may be infected into the inner space of the balloon and through which the fluid may be discharged from the inner space of the balloon is a single flexible tube.

11. The hood according to claim 10, wherein the flexible tube is arranged on, and attached to, an outer side of the insertion section of the endoscope.

12. The hood according to claim 1, wherein the balloon, together with the body member, is adapted to be detachably mounted on the distal end portion of the insertion section of the endoscope.

13. The hood according to claim 1, wherein said inner circumferential surface comprises an inelastic portion and said outer circumferential surface comprises an elastic portion.

14. A hood adapted to be mounted at a distal end portion of an insertion section of an endoscope, said hood comprising:

a body member having an opening at a distal end side;

an annular balloon mounted on the body member and having an inner space, said balloon being adapted to be expanded by injecting a fluid into the inner space so that at least an external diameter is enlarged and to be contracted by discharging the fluid out of the inner space so that the balloon is shrunk to a substantially cylindrical configuration; and at least one passageway through which the fluid may be injected into the inner space of the balloon, and through which the fluid may be discharged out of the inner space of the balloon;

wherein said balloon comprises a rearward inner surface portion connected to an outer peripheral surface of the body member; and wherein a small-diameter annular section is formed on an inner side of a forward end opening of the balloon, and when the balloon is expanded the small-diameter annular section is adapted to anchor a high-frequency snare wire and hold the wire in place.

15. A hood adapted to be mounted at a distal end portion of an insertion section of an endoscope, said hood comprising:

a body member having an opening at a distal end side;

an annular balloon mounted on the body member and having an inner space, said balloon being adapted to be expanded by injecting a fluid into the inner space so that at least an external diameter is enlarged and to be contracted by discharging the fluid out of the inner space so that the balloon is shrunk to a substantially cylindrical configuration; and at least one passageway through which the fluid may be injected into the inner space of the balloon, and through which the fluid may be discharged out of the inner space of the balloon;

wherein said balloon comprises a rearward inner surface portion connected to an outer peripheral surface of the body member;

wherein said balloon comprises a portion which, when the balloon is expanded by injecting the fluid into the inner space, extends forward relative to a forward end of the body member and is expanded into a substantially annular configuration so that an observation space and operation field can be secured; and wherein a small-diameter annular section is formed on an inner side of a forward end opening of the portion of the balloon expanded into the substantially annular configuration, and said small-diameter annular section is adapted to anchor a looped high-frequency snare wire and hold the wire in place.

16. A hood adapted to be mounted at a distal end portion of an insertion section of an endoscope, said hood comprising:

a body member having an opening at a distal end side;

an annular balloon mounted on the body member and having an inner space, said balloon being adapted to be expanded by injecting a fluid into the inner space so that at least an external diameter is enlarged and to be contracted by discharging the fluid out of the inner space so that the balloon is shrunk to a substantially cylindrical configuration; and at least one passageway through which the fluid may be injected into the inner space of the balloon, and through which the fluid may be discharged out of the inner space of the balloon;

wherein said balloon comprises a rearward inner surface portion connected to an outer peripheral surface of the body member; and wherein said balloon comprises an inelastic inner peripheral surface portion and an elastic outer peripheral surface portion.

\* \* \* \* \*